United States Patent [19]
Ito et al.

[11] Patent Number: 5,691,276
[45] Date of Patent: Nov. 25, 1997

[54] HERBICIDAL COMPOSITION COMPRISING A FLUOROPROPYLTHIAZOLINE SULFONYLUREA DERIVATIVE AND ANOTHER HERBICIDE

[75] Inventors: Yoichi Ito; Kazuhisa Sudo; Tsutomu Nawamaki, all of Shiraoka-machi; Kenzi Makino, Funabashi, all of Japan

[73] Assignee: Nissan Chemical Corporation, Tokyo, Japan

[21] Appl. No.: 750,782

[22] PCT Filed: Jun. 22, 1995

[86] PCT No.: PCT/JP95/01251

§ 371 Date: Dec. 20, 1996

§ 102(e) Date: Dec. 20, 1996

[87] PCT Pub. No.: WO91/00009

PCT Pub. Date: Jan. 4, 1996

[30] Foreign Application Priority Data

Jun. 23, 1994 [JP] Japan ..................... 6-141445

[51] Int. Cl.$^6$ .......... A01N 43/66; A01N 43/78; A01N 47/36
[52] U.S. Cl. .......................... 504/134; 504/135
[58] Field of Search ..................... 504/134, 135

[56] References Cited

PUBLICATIONS

CA 126:74875. Abstract of JP 08–277289, 22 Oct. 1996.
CA 123:228210. Abstract of WO 95–18806, 13 Jul. 1995.
CA 124:289581. Abstract of JP 07–330765, 19 Dec. 1995.
CA 124:176080. Abstract of JP 07–278144, 24 Oct. 1995.

*Primary Examiner*—S. Mark Clardy
*Attorney, Agent, or Firm*—Oblon, Spivak, McClelland, Maier & Neustadt, P.C.

[57] ABSTRACT

A mixture of a compound represented by the formula (1) and at least one compound selected from the group consisting of phenmedipham, ethofumesate, chloridazon, metamitron and triflusulfuron-methyl, which is safe for sugar beet and has excellent properties.

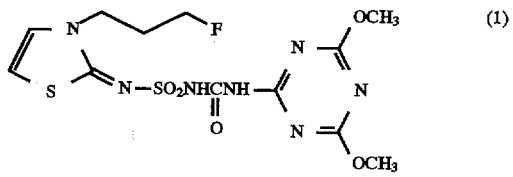

6 Claims, No Drawings

HERBICIDAL COMPOSITION COMPRISING A FLUOROPROPYLTHIAZOLINE SULFONYLUREA DERIVATIVE AND ANOTHER HERBICIDE

This application has been filed under 35 USC 371 as a national stage application of PCT/JP 95/01251, filed Jun. 22, 1995.

TECHNICAL FIELD

The present invention relates to a herbicidal composition containing a fluoropropylthiazoline derivative and a certain type of herbicide as active ingredients.

BACKGROUND ART

Many years of research and development of herbicides brought a great variety of chemicals into practical use, and these herbicides have contributed to labor saving in weed control and the improvement in the productivity of farm and garden crops. Even in these days, development of new chemicals having more excellent herbicidal properties is still demanded. As agricultural and horticultural herbicides, chemicals which selectively control the target weeds at low doses without showing phytotoxicity to crop plants are particularly desired. However, no existing chemicals satisfy all these desired conditions.

The compound represented by the following formula (1) in the present invention [hereinafter referred to as compound (1)], which was disclosed in International Patent Application PCT/JP95/00011, is a herbicide which shows an excellent herbicidal effect on Graminaceous weeds such as wild oat and blackgrass and broad-leaved weeds such as common lambsquater, common chickweed, kedlock and slender amaranth at low doses in foliage treatment and is fairly safe for sugar beet, but does not have much effect on some broad-leaved weeds.

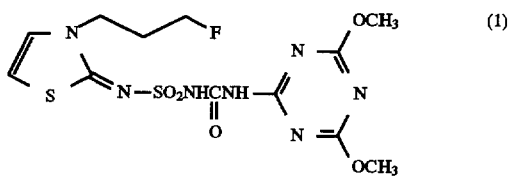

(1)

On the other hand, the compound represented by the following formula (2) [hereinafter referred to as compound (2)], the compound represented by the formula (3) [hereinafter referred to as compound (3)], the compound represented by the formula (4) [hereinafter referred to as compound (4)], the compound represented by the formula (5) [hereinafter referred to as compound (5)] and the compound represented by the formula (6) [hereinafter referred to as compound (6)] are already known and in practical use as herbicides for sugar beet, but have a drawback that they don't have much effect on Graminaceous weeds or some broad-leaved weeds.

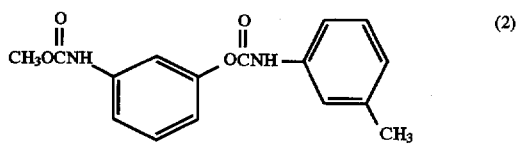

(2)

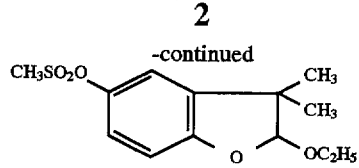

(3)

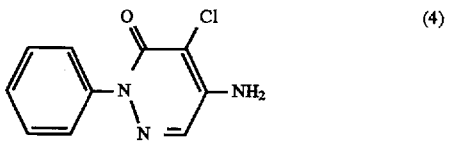

(4)

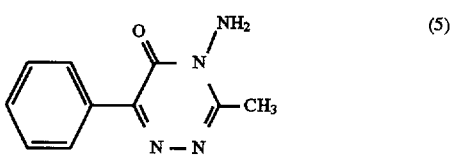

(5)

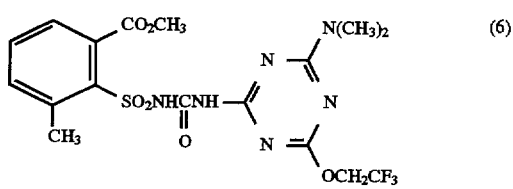

(6)

DISCLOSURE OF THE INVENTION

The present inventors found combined use of compound (1) and at least one compound selected from the group consisting of compound (2), compound (3), compound (4), compound (5) and compound (6) not only compensates for the drawbacks of the individual compounds used in single formulation but also enables reduction in the application dose and simultaneous control of Graminaceous weeds and broad-leaved weeds. The present invention has been accomplished on the basis of this discovery.

The common name of compound (2) in the present invention is phenmedipham, the common name of compound (3) is ethofumesate, the common name of compound (4) is chloridazon, the common name of compound (5) is metamitron, and the common name of compound (6) is triflusulfuron-methyl (test name DPX-66037).

In addition to compound (2), compound (3), compound (4), compound (5) and compound (6), the following compounds may be mentioned as a herbicide which can be used in combination with compound (1). Examples of such formulations will be given later in Formulation Examples 26 to 39.

It is also possible to add one or two of the following compounds to a mixture of compound (1) and at least one compound selected from the group consisting of compound (2), compound (3), compound (4), compound (5) and compound (6).

Desmedipham (common name), cycloate (common name), diallate (common name), lenacil (common name), TCA, pebulate (common name), endothal (common name), EPTC, fluazifop-P-butyl (common name), sethoxydim (common name), haloxyfop-methyl (common name), quizalofop-ethyl (common name), trifluralin (common name), diethatyl-ethyl (common name) and the like may be mentioned. Examples of such formulations will be given later in Formation Examples 40 to 56.

Addition of such a chemical to compound (1) or to a mixture of compound (1) and one of compounds (2) to (6) is expected to lead to, for instance, a broad weeding spectrum, a reduced application dose and persistent herbicidal effect.

In the present invention, compound (1) and one of compounds (2) to (6) are used in an appropriate ratio selected from such a range that the two chemicals do not impair each other's performance.

For example, one of compounds (2) to (6) is used preferably in an amount of from 0.01 to 500 parts by weight, more preferably from 0.1 to 100 parts by weight per 1 part by weight of compound (1).

When the herbicidal composition of the present invention is used as a herbicide, it is usually mixed with a suitable carrier, for instance, a solid carrier such as clay, talc, bentonite, diatomaceous earth or white carbon, or a liquid carrier such as water, an alcohol (such as isopropanol, butanol, benzyl alcohol or furfuryl alcohol), an aromatic hydrocarbon (such as toluene or xylene), an ether (such as an anisole), a ketone (such as cyclohexanone or isophorone), an ester (such as butyl acetate), an acid amide (such as N-methylpyrrolidone) or a halogenated hydrocarbon (such as chlorobenzene). If desired, a surfactant, an emulsifier, a dispersing agent, a penetrating agent, a spreader, a thickener, an antifreezing agent, an anticaking agent or a stabilizer may be added to prepare an optional formulation such as a liquid formulation, an emulsifiable concentrate, a wettable powder, a dry flowable, a flowable, a dust or a granule.

The herbicidal composition of the present invention is fairly safe for sugar beet and effectively controls Graminaceous weeds and broad-leaved weeds, which are harmful to cultivation of sugar beet.

Now, examples of formulations of the herbicidal composition of the present invention will be given below. However, it should be understood that the present invention is by no means restricted to such specific examples.

In the following, "parts" means "parts by weight".
[Formulation Example 1] Wettable powder

| | |
|---|---|
| Compound (1) | 3.5 parts |
| Compound (2) | 28 parts |
| Zeeklite PFP | 61.5 parts |
| (Tradename for a kaolin-type clay, manufactured by Zeeklite Industries, Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 2 parts |
| (Tradename for a white carbon, manufactured by Shionogi Pharmaceutical Co., Ltd.) | |

The above ingredients were homogeneously pulverized and mixed to form a wettable powder. [Formulation Example 2] Wettable powder

| | |
|---|---|
| Compound (1) | 1 part |
| Compound (3) | 30 parts |
| Zeeklite PFP | 62 parts |
| (Tradename for a kaolin-type clay, manufactured by Zeeklite Industries, Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 2 parts |
| (Tradename for a white carbon, manufactured by Shionogi Pharmaceutical Co., Ltd.) | |

The above ingredients were homogeneously pulverized and mixed to form a wettable powder. [Formulation Example 3] Wettable powder

| | |
|---|---|
| Compound (1) | 0.5 part |
| Compound (4) | 30 parts |
| Zeeklite PFP | 62.5 parts |
| (Tradename for a kaolin-type clay, manufactured by Zeeklite Industries, Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 2 parts |
| (Tradename for a white carbon, manufactured by Shionogi Pharmaceutical Co., Ltd.) | |

The above ingredients were homogeneously pulverized and mixed to form a wettable powder. [Formulation Example 4] Wettable powder

| | |
|---|---|
| Compound (1) | 0.5 part |
| Compound (5) | 30 parts |
| Zeeklite PFP | 62.5 parts |
| (Tradename for a kaolin-type clay, manufactured by Zeeklite Industries, Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 2 parts |
| (Tradename for a white carbon, manufactured by Shionogi Pharmaceutical Co., Ltd.) | |

The above ingredients were homogeneously pulverized and mixed to form a wettable powder. [Formulation Example 5] Wettable powder

| | |
|---|---|
| Compound (1) | 15 parts |
| Compound (6) | 15 parts |
| Zeeklite PFP | 63 parts |
| (Tradename for a kaolin-type clay, manufactured by Zeeklite Industries, Co., Ltd.) | |
| Sorpol 5050 | 2 parts |
| (Tradename for an anionic surfactant, manufactured by Toho Chemical Industry Co., Ltd.) | |
| Lunox 1000 | 3 parts |
| (Tradename for an anionic surfactant, manufactured by Toho Chemical Industry Co., Ltd.) | |
| Carplex #80 (anticaking agent) | 2 parts |
| (Tradename for a white carbon, manufactured by Shionogi Pharmaceutical Co., Ltd.) | |

The above ingredients were homogeneously pulverized and mixed to form a wettable powder. [Formation Example 6] Emulsifiable concentrate

| | |
|---|---|
| Compound (1) | 0.5 part |
| compound (2) | 4 parts |
| Xylene | 74.5 parts |
| Isophorone | 15 parts |
| Sorpol 3005X | 6 parts |
| (Tradename for a mixture of nonionic and anionic surfactants, manufactured by Toho Chemical Industry Co., Ltd.) | |

The above ingredients were homogeneously pulverized and mixed to form an emulsifiable concentrate. [Formation Example 7] Emulsifiable concentrate

| | |
|---|---|
| Compound (1) | 0.2 part |
| compound (3) | 6 parts |
| Xylene | 72.8 parts |
| Isophorone | 15 parts |
| Sorpol 3005X | 6 parts |
| (Tradename for a mixture of nonionic and anionic surfactants, manufactured by Toho Chemical Industry Co., Ltd.) | |

The above ingredients were homogeneously pulverized and mixed to form an emulsifiable concentrate. [Formation Example 8] Emulsifiable concentrate

| | |
|---|---|
| Compound (1) | 0.1 part |
| compound (4) | 6 parts |
| Xylene | 72.9 parts |
| Isophorone | 15 parts |
| Sorpol 3005X | 6 parts |
| (Tradename for a mixture of nonionic and anionic surfactants, manufactured by Toho Chemical Industry Co., Ltd.) | |

The above ingredients were homogeneously pulverized and mixed to form an emulsifiable concentrate. [Formation Example 9] Emulsifiable concentrate

| | |
|---|---|
| Compound (1) | 0.1 part |
| compound (5) | 6 parts |
| Xylene | 72.9 parts |
| Isophorone | 15 parts |
| Sorpol 3005X | 6 parts |
| (Tradename for a mixture of nonionic and anionic surfactants, manufactured by Toho Chemical Industry Co., Ltd.) | |

The above ingredients were homogeneously pulverized and mixed to form an emulsifiable concentrate. [Formation Example 10] Emulsifiable concentrate

| | |
|---|---|
| Compound (1) | 2.5 parts |
| compound (6) | 2.5 parts |
| Xylene | 74 parts |
| Isophorone | 15 parts |
| Sorpol 3005X | 6 parts |
| (Tradename for a mixture of nonionic and anionic surfactants, manufactured by Toho Chemical Industry Co., Ltd.) | |

The above ingredients were homogeneously pulverized and mixed to form an emulsifiable concentrate. [Formulation Example 11] Flowable

| | |
|---|---|
| Compound (1) | 5 parts |
| Compound (2) | 40 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 18.5 parts |

The above ingredients were homogeneously mixed to form a flowable. [Formulation Example 12] Flowable

| | |
|---|---|
| Compound (1) | 1.5 parts |
| Compound (3) | 45 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 17 parts |

The above ingredients were homogeneously mixed to form a flowable. [Formulation Example 13] Flowable

| | |
|---|---|
| Compound (1) | 0.75 part |
| Compound (4) | 45 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 17.75 parts |

The above ingredients were homogeneously mixed to form a flowable. [Formulation Example 14] Flowable

| | |
|---|---|
| Compound (1) | 0.75 part |
| Compound (5) | 45 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 17.75 parts |

The above ingredients were homogeneously mixed to form a flowable. [Formulation Example 15] Flowable

| | |
|---|---|
| Compound (1) | 20 parts |
| Compound (6) | 20 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône- | |

Poulenc)
Ethylene glycol (anti-freezing agent) 8 parts
Water 23.5 parts

The above ingredients were homogeneously mixed to form a flowable. [Formulation Example 16] Granular wettable powder (dry flowable)

| Compound (1) | 8 parts |
|---|---|
| Compound (2) | 64 parts |
| Isoban No. 1 | 10 parts |
| (Tradename for an anionic surfactant, manufactured by Kuraray Isoprene Chemical Co., Ltd.) | |
| Vanilex N | 5 parts |
| (Tradename for an anionic surfactant, manufactured by Sanyo-Kokusaku Pulp Co. Ltd.) | |
| Carplex #80 | 13 parts |
| (Tradename for a white carbon, manufactured by Shionogi Pharmaceutical Co., Ltd.) | |

The above ingredients were homogeneously pulverized and mixed to form a dry flowable. [Formulation Example 17] Granular wettable powder (dry flowable)

| Compound (1) | 2.5 parts |
|---|---|
| Compound (3) | 75 parts |
| Isoban No. 1 | 10 parts |
| (Tradename for an anionic surfactant, manufactured by Kuraray Isoprene Chemical Co., Ltd.) | |
| Vanilex N | 5 parts |
| (Tradename for an anionic surfactant, manufactured by Sanyo-Kokusaku Pulp Co. Ltd.) | |
| Carplex #80 | 7.5 parts |
| (Tradename for a white carbon, manufactured by Shionogi Pharmaceutical Co., Ltd.) | |

The above ingredients were homogeneously pulverized and mixed to form a dry flowable. [Formulation Example 18] Granular wettable powder (dry flowable)

| Compound (1) | 1.2 parts |
|---|---|
| Compound (4) | 72 parts |
| Isoban No. 1 | 10 parts |
| (Tradename for an anionic surfactant, manufactured by Kuraray Isoprene Chemical Co., Ltd.) | |
| Vanilex N | 5 parts |
| (Tradename for an anionic surfactant, manufactured by Sanyo-Kokusaku Pulp Co. Ltd.) | |
| Carplex #80 | 11.8 parts |
| (Tradename for a white carbon, manufactured by Shionogi Pharmaceutical Co., Ltd.) | |

The above ingredients were homogeneously pulverized and mixed to form a dry flowable. [Formulation Example 19] Granular wettable powder (dry flowable)

| Compound (1) | 1.2 parts |
|---|---|
| Compound (5) | 72 parts |
| Isoban No. 1 | 10 parts |
| (Tradename for an anionic surfactant, manufactured by Kuraray Isoprene Chemical Co., Ltd.) | |
| Vanilex N | 5 parts |
| (Tradename for an anionic surfactant, manufactured by Sanyo-Kokusaku Pulp Co. Ltd.) | |
| Carplex #80 | 11.8 parts |
| (Tradename for a white carbon, manufactured by Shionogi Pharmaceutical Co., Ltd.) | |

The above ingredients were homogeneously pulverized and mixed to form a dry flowable. [Formulation Example 20] Granular wettable powder (dry flowable)

| Compound (1) | 38 parts |
|---|---|
| Compound (6) | 38 parts |
| Isoban No. 1 | 10 parts |
| (Tradename for an anionic surfactant, manufactured by Kuraray Isoprene Chemical Co., Ltd.) | |
| Vanilex N | 5 parts |
| (Tradename for an anionic surfactant, manufactured by Sanyo-Kokusaku Pulp Co. Ltd.) | |
| Carplex #80 | 9 parts |
| (Tradename for a white carbon, manufactured by Shionogi Pharmaceutical Co., Ltd.) | |

The above ingredients were homogeneously pulverized and mixed to form a dry flowable. [Formulation Example 21] Granule

| Compound (1) | 0.05 part |
|---|---|
| Compound (2) | 0.4 part |
| Bentonite | 50.0 parts |
| Talc | 44.55 parts |
| Toxanone GR-31A | 5 parts |
| (Tradename for an anionic surfactant, manufactured by Sanyo Chemical Industries, Ltd.) | |

The above ingredients were homogeneously mixed and pulverized, and after addition of a small amount of water, the mixture was kneaded, mixed and granulated by an extrusion-type granulating machine, followed by drying to obtain a granule. [Formulation Example 22] Granule

| Compound (1) | 0.015 part |
|---|---|
| Compound (3) | 0.45 part |
| Bentonite | 50.0 parts |
| Talc | 44.535 parts |
| Toxanone GR-31A | 5 parts |
| (Tradename for an anionic surfactant, manufactured by Sanyo Chemical Industries, Ltd.) | |

The above ingredients were homogeneously mixed and pulverized, and after addition of a small amount of water, the mixture was kneaded, mixed and granulated by an extrusion-type granulating machine, followed by drying to obtain a granule. [Formulation Example 23] Granule

| Compound (1) | 0.01 part |
|---|---|
| Compound (4) | 0.6 part |
| Bentonite | 50.0 parts |
| Talc | 44.39 parts |
| Toxanone GR-31A | 5 parts |
| (Tradename for an anionic surfactant, manufactured by Sanyo Chemical Industries, Ltd.) | |

The above ingredients were homogeneously mixed and pulverized, and after addition of a small amount of water, the mixture was kneaded, mixed and granulated by an extrusion-type granulating machine, followed by drying to obtain a granule. [Formulation Example 24] Granule

| | |
|---|---|
| Compound (1) | 0.01 part |
| Compound (5) | 0.6 part |
| Bentonite | 50.0 parts |
| Talc | 44.39 parts |
| Toxanone GR-31A | 5 parts |
| (Tradename for an anionic surfactant, manufactured by Sanyo Chemical Industries, Ltd.) | |

The above ingredients were homogeneously mixed and pulverized, and after addition of a small amount of water, the mixture was kneaded, mixed and granulated by an extrusion-type granulating machine, followed by drying to obtain a granule. [Formulation Example 25] Granule

| | |
|---|---|
| Compound (1) | 0.25 part |
| Compound (6) | 0.25 part |
| Bentonite | 50.0 parts |
| Talc | 44.5 parts |
| Toxanone GR-31A | 5 parts |
| (Tradename for an anionic surfactant, manufactured by Sanyo Chemical Industries, Ltd.) | |

The above ingredients were homogeneously mixed and pulverized, and after addition of a small amount of water, the mixture was kneaded, mixed and granulated by an extrusion-type granulating machine, followed by drying to obtain a granule. [Formulation Example 26] Flowable

| | |
|---|---|
| Compound (1) | 4 parts |
| Desmedipham | 40 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 19.5 parts |

The above ingredients were homogeneously mixed to form a flowable. [Formulation Example 27] Wettable powder

| | |
|---|---|
| Compound (1) | 0.5 part |
| Cycloate | 30 parts |
| Zeeklite PFP | 44.5 parts |
| (Tradename for a kaolin-type clay, manufactured by Zeeklite Industries Co. Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 28] Wettable powder

| | |
|---|---|
| Compound (1) | 1 part |
| Diallate | 30 parts |
| Zeeklite PFP | 44 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 29] Flowable

| | |
|---|---|
| Compound (1) | 2.5 parts |
| Lenacil | 40 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 21 parts |

The above ingredients were homogeneously mixed to form a flowable. [Formulation Example 30] Flowable

| | |
|---|---|
| Compound (1) | 0.4 part |
| TCA | 40 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 23.1 parts |

The above ingredients were homogeneously mixed to form a flowable. [Formulation Example 31] Wettable powder

| | |
|---|---|
| Compound (1) | 0.75 part |
| Pebulate | 30 parts |
| Zeeklite PFP | 44.25 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 32] Flowable

| | |
|---|---|
| Compound (1) | 2 parts |
| Endothal | 40 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 21.5 parts |

The above ingredients were homogeneously mixed to form a flowable. [Formulation Example 33] Wettable powder

| | |
|---|---|
| Compound (1) | 0.75 part |
| EPTC | 30 parts |
| Zeeklite PFP | 44.25 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 34] Wettable powder

| | |
|---|---|
| Compound (1) | 8 parts |
| Fluazifop-P-butyl | 20 parts |
| Zeeklite PFP | 47 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 35] Wettable powder

| | |
|---|---|
| Compound (1) | 4 parts |
| Sethoxydim | 32 parts |
| Zeeklite PFP | 39 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |

-continued

| | |
|---|---|
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 36] Flowable

| | |
|---|---|
| Compound (1) | 7 parts |
| Haloxyfop-methyl | 39.2 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 17.3 parts |

The above ingredients were homogeneously mixed to form a flowable. [Formulation Example 37] Flowable

| | |
|---|---|
| Compound (1) | 20 parts |
| Quizalofop-ethyl | 20 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 23.5 parts |

The above ingredients were homogeneously mixed to form a flowable. [Formulation Example 38] Flowable

| | |
|---|---|
| Compound (1) | 4 parts |
| Trifluralin | 40 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 19.5 parts |

The above ingredients were homogeneously mixed to form a flowable. [Formulation Example 39] Flowable

| | |
|---|---|
| Compound (1) | 2 parts |
| Diethatyl-ethyl | 40 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |

| | |
|---|---|
| (Tradename for a thickener, manufactured by Rhône-Poulenc) | |
| Ethylene glycol (anti-freezing agent) | 8 parts |
| Water | 21.5 parts |

The above ingredients were homogeneously mixed to form a flowable. [Formulation Example 40] Wettable powder

| | |
|---|---|
| Compound (1) | 0.75 part |
| Compound (2) | 6 parts |
| Diallate | 22.5 parts |
| Zeeklite PFP | 45.75 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 41] Wettable powder

| | |
|---|---|
| Compound (1) | 2.6 parts |
| Compound (2) | 20.8 parts |
| Fluazifop-P-butyl | 6.5 parts |
| Zeeklite PFP | 45.1 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 42] Wettable powder

| | |
|---|---|
| Compound (1) | 1.8 parts |
| Compound (2) | 14.4 parts |
| Sethoxydim | 14.4 parts |
| Zeeklite PFP | 44.4 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 43] Flowable

| | |
|---|---|
| Compound (1) | 2.8 parts |
| Compound (2) | 22.4 parts |
| Haloxyfop-methyl | 15.68 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 22.62 parts |

The above ingredients were homogeneously mixed to form a flowable. [Formulation Example 44] Flowable

| | |
|---|---|
| Compound (1) | 4 parts |
| Compound (2) | 32 parts |
| Quizalofop-ethyl | 4 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 23.5 parts |

The above ingredients were homogeneously mixed to form a flowable. [Formulation Example 45] Flowable

| | |
|---|---|
| Compound (1) | 2 parts |
| Compound (2) | 16 parts |
| Trifluralin | 20 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 25.5 parts |

The above ingredients were homogeneously mixed to form a flowable. [Formulation Example 46] Flowable

| | |
|---|---|
| Compound (1) | 1.4 parts |
| Compound (2) | 11.2 parts |
| Diethatyl-ethyl | 28 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 22.9 parts |

The above ingredients were homogeneously mixed to form a flowable. [Formulation Example 47] Wettable powder

| | |
|---|---|
| Compound (1) | 0.8 part |
| Compound (3) | 24 parts |
| Sethoxydim | 6.4 parts |
| Zeeklite PFP | 43.8 parts |
| (Tradename for a kaolin-type clay, manufactured by Zeeklite Industries Co., Ltd.) | |
| Sorpol 5050 | 2 parts |
| (Tradename for an anionic surfactant manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 48] Flowable

| | |
|---|---|
| Compound (1) | 1.25 parts |
| Compound (3) | 37.5 parts |
| Quizalofop-ethyl | 1.25 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 23.5 parts |

The above ingredients were homogeneously mixed to form a flowable. [Formulation Example 49] Wettable powder

| | |
|---|---|
| Compound (1) | 0.5 part |
| Compound (4) | 30 parts |
| Sethoxydim | 4 parts |
| Zeeklite PFP | 40.5 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 50] Flowable

| | |
|---|---|
| Compound (1) | 0.65 part |
| Compound (4) | 39 parts |
| Quizalofop-ethyl | 0.65 part |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 23.2 parts |

The above ingredients were homogeneously mixed to form a flowable. [Formulation Example 51] Wettable powder

| | |
|---|---|
| Compound (1) | 0.5 part |
| Compound (5) | 30 parts |
| Sethoxydim | 4 parts |
| Zeeklite PFP | 40.5 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 52] Flowable

| | |
|---|---|
| Compound (1) | 0.65 part |
| Compound (5) | 39 parts |
| Quizalofop-ethyl | 0.65 part |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 23.2 parts |

The above ingredients were homogeneously mixed to form a flowable. [Formulation Example 53] Wettable powder

| | |
|---|---|
| Compound (1) | 7 parts |
| Compound (6) | 7 parts |
| Fluazifop-P-butyl | 17.5 parts |
| Zeeklite PFP | 43.5 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 54] Wettable powder

| | |
|---|---|
| Compound (1) | 3 parts |
| Compound (6) | 3 parts |
| Sethoxydim | 24 parts |
| Zeeklite PFP | 45 parts |
| (Tradename for a kaolin-type clay, manufactured by Zeeklite Industries Co., Ltd.) | |
| Sorpol 5050 | 2 parts |
| (Tradename for an anionic surfactant, manufactured by Toho Chemical Industry Co., Ltd.) | |
| Lunox 1000C | 3 parts |
| (Tradename for an anionic surfactant, manufactured by Toho Chemical Industry Co., Ltd.) | |
| Carplex #80 (anticaking agent) | 20 parts |
| (Tradename for a white carbon, manufactured by Shionogi Pharmaceutical Co., Ltd.) | |

The above ingredients were homogeneously pulverized and mixed to form a wettable powder. [Formulation Example 55] Flowable

| | |
|---|---|
| Compound (1) | 6 parts |
| Compound (6) | 6 parts |
| Haloxyfop-methyl | 33.6 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 17.9 parts |

The above ingredients were homogeneously mixed to form a flowable. [Formulation Example 56] Flowable

| | |
|---|---|
| Compound (1) | 15 parts |
| Compound (6) | 15 parts |
| Quizalofop-ethyl | 15 parts |
| Agrizole S-711 | 8 parts |
| (Tradename for a nonionic surfactant, manufactured by Kao Corporation) | |
| Lunox 1000C | 0.5 part |
| (Tradename for an anionic surfactant, manufactured by Toho Chemical Industry Co., Ltd.) | |
| 1% Rodopol water | 20 parts |
| (Tradename for a thickener, manufactured by Rhône-Poulenc) | |
| Ethylene glycol (anti-freezing agent) | 8 parts |
| Water | 18.5 parts |

The above ingredients were homogeneously mixed to form a flowable.

Now, the following Text Examples are given to demonstrate that the combination of compound (1) with one of compounds (2) to (6) has a more excellent effect than their single formulations anticipate, namely has a synergic effect.

TEST EXAMPLE 1

Plastic box having a length of 33 cm, a width of 33 cm and a depth of 8 cm were filled with sterilized diluvial soil, and slender amaranth was sown at a depth of about 1.5 cm dep in each box. The plant was grown in a greenhouse at a temperature of from 20° to 25° C. for 14 days and then treated with chemicals. Wettable powders of compound (1), compound (2), compound (3) and their mixtures were suspended and diluted with water to predetermined concentrations, and 10 ml of each suspension was uniformly applied to the foliage. The plant was grown in the plastic boxes placed in a greenhouse. 28 Days after the treatment, the aerial parts of slender amaranth were weighed, and the control rates (Eo) were calculated from the following formula.

$$Eo(\%) = [1 - (\text{the weight of the plant in a treated area/the weight of the plant in the non-treated area})] \times 100$$

Although individual active compounds usually have drawbacks in their herbicidal activities, the herbicidal effect of a mixture of two active compounds can exceed the simple sum of the effects of the individual compounds (the expected control rate). In such a case, it is called synergy. The expected control rate Ec of a specific combination of two herbicides is calculated as follows (Colby S. R., calculation of synergic and antagonistic effects of herbicide combinations, "Weed", vol. 15, pp. 20–22, 1967).

$$Ec = \alpha + \beta - (\alpha \cdot \beta)/100$$

α: The control rate of herbicide A applied at a rate of (a) kg/ha.

β: The control rate of herbicide B applied at a rate of (b) kg/ha.

Ec: The expected control rate of herbicide A applied at a rate of (a) kg/ha and herbicide B applied at a rate of (b) kg/ha.

Namely, when Eo is larger than Ec, the effect of the herbicide combination is considered as synergy.

The results are shown in Table 1 and Table 2. The symbol in the Tables has the following meaning.

A: Slender amaranth

TABLE 1

Herbicidal effects of single formulations (control rate %)

| Compound | Application rate of active ingredient (g/a) | A |
|---|---|---|
| Compound (1) | 0.1 | 71 |
| | 0.2 | 81 |
| | 0.4 | 85 |
| Compound (2) | 1.6 | 0 |
| | 3.2 | 0 |
| | 6.4 | 5 |
| Compound (3) | 1.6 | 0 |
| | 3.2 | 9 |
| | 6.4 | 38 |

TABLE 2

Actual and expected herbicidal effects of mixtures (control rate %)

| Application rate of active ingredient (g/a) | | | A Actual value | Expected value |
|---|---|---|---|---|
| Comp.(1) | + | Comp. (2) | | |
| 0.1 | + | 1.6 | 85 | 71 |
| 0.1 | + | 3.2 | 85 | 71 |
| 0.1 | + | 6.4 | 85 | 72 |
| 0.2 | + | 1.6 | 90 | 81 |
| 0.2 | + | 3.2 | 90 | 81 |
| 0.2 | + | 6.4 | 92 | 82 |
| 0.4 | + | 1.6 | 95 | 85 |

TABLE 2-continued

Actual and expected herbicidal effects of mixtures (control rate %)

| Application rate of active ingredient (g/a) | | | A Actual value | Expected value |
|---|---|---|---|---|
| 0.4 | + | 3.2 | 98 | 85 |
| 0.4 | + | 6.4 | 100 | 86 |
| Comp. (1) | + | Comp. (3) | | |
| 0.1 | + | 1.6 | 84 | 71 |
| 0.1 | + | 3.2 | 86 | 74 |
| 0.1 | + | 6.4 | 89 | 82 |
| 0.2 | + | 1.6 | 90 | 81 |
| 0.2 | + | 3.2 | 90 | 83 |
| 0.2 | + | 6.4 | 93 | 88 |
| 0.4 | + | 1.6 | 95 | 85 |
| 0.4 | + | 3.2 | 95 | 86 |
| 0.4 | + | 6.4 | 98 | 91 |

(The expected values in the table are calculated from Colby's equation, which is mentioned above.)

From the results in Table 2, it is evident that mixtures of compound (1) with compound (2) and compound (3) have effects exceeding the expected values and act synergically on slender amaranth.

TEST EXAMPLE 2

Plastic boxes having a length of 33 cm, a width of 33 cm and a depth of 8 cm were filled with sterilized diluvial soil, and tufted knotweed was sown at a depth of about 1.5 cm. The plant was grown in a greenhouse at a temperature of from 20° to 25° C. and then treated with chemicals. Wettable powders of compound (1), compound (4), compound (5) and their mixtures were suspended and diluted with water to predetermined concentrations, and then 10 ml of each suspension was uniformly applied to the foliage. The plant was grown the plastic box is placed in a greenhouse. 28 Days after the application, the aerial parts of tufted knotweed were weighed, and the control rates (Eo) were calculated in the same manner as in Test Example 1. The results are shown in Table 3 and Table 4. The symbol in the Tables has the following meaning.

B: Tufted knotweed

TABLE 3

Herbicidal effects of single formulations (control rate %)

| Compound | Application rate of active ingredient (g/a) | B |
|---|---|---|
| Compound (1) | 0.1 | 62 |
| | 0.2 | 71 |
| | 0.4 | 80 |
| Compound (4) | 1.6 | 29 |
| | 3.2 | 66 |
| | 6.4 | 100 |
| Compound (5) | 1.6 | 0 |
| | 3.2 | 30 |
| | 6.4 | 43 |

TABLE 4

Actual and expected herbicidal effects of mixtures (control rate %)

| Application rate of active ingredient (g/a) | | | B Actual value | Expected value |
|---|---|---|---|---|
| Comp. (1) | + | Comp.(4) | | |
| 0.1 | + | 1.6 | 80 | 73 |
| 0.1 | + | 3.2 | 93 | 87 |
| 0.1 | + | 6.4 | 100 | 100 |
| 0.2 | + | 1.6 | 85 | 79 |
| 0.2 | + | 3.2 | 95 | 90 |
| 0.2 | + | 6.4 | 100 | 100 |
| 0.4 | + | 1.6 | 89 | 86 |
| 0.4 | + | 3.2 | 100 | 93 |
| 0.4 | + | 6.4 | 100 | 100 |
| Comp. (1) | + | Comp. (5) | | |
| 0.1 | + | 1.6 | 73 | 62 |
| 0.1 | + | 3.2 | 80 | 73 |
| 0.1 | + | 6.4 | 83 | 78 |
| 0.2 | + | 1.6 | 83 | 71 |
| 0.2 | + | 3.2 | 85 | 80 |
| 0.2 | + | 6.4 | 90 | 83 |
| 0.4 | + | 1.6 | 83 | 80 |
| 0.4 | + | 3.2 | 90 | 86 |
| 0.4 | + | 6.4 | 95 | 89 |

(The expected values in the table are calculated from Colby's equation, which is mentioned above.)

The results in Table 4 clearly indicate that mixtures of compound (1) with compound (4) and compound (5) have effects exceeding the expected values and act synergically on tufted knotweed.

TEST EXAMPLE 3 Herbicidal effects and phytotoxicity test

Plastic boxes having a length of 33 cm, a width of 33 cm and a depth of 8 cm were filled with sterilized diluvial soil, and sugar beet, wild oat, blackgrass, common lambsquater, common chickweed, kedlock, tufted knotweed and slender amaranth were sown in each box at a depth of about 1.5 cm. The plants were grown in a greenhouse at a temperature of from 20° to 25° C. for 14 days and then the flowables prepared in accordance with Formulation Example 11, Formulation Example 12, Formulation Example 13, Formulation Example 14 and Formulation Example 15 were diluted with water and applied uniformly to the foliage. 28 Days after the application, the effects on respective weeds and sugar beet were evaluated on the basis of the following standard ratings.

Standard ratings

5: Complete destruction or control rate of more than 90%

4: Control rate of from 70 to 90%

3: Control rate of from 40 to 70%

2: Control rate of from 20 to 40%

1: Control rate of from 5 to 20%

0: Control rate of less than 5%

The results are shown in Table 5. The symbols in the Table have the following meanings.

A: sugar beet, B: wild oat, C: blackgrass, D: common lambsquater, E: common chickweed, F: kedlock, G: tufted knotweed, H: slender amaranth

TABLE 5

Herbicidal effect and phytotoxicity against sugar beet

| | Application rate of flowable (g/a) | A | B | C | D | E | F | G | H |
|---|---|---|---|---|---|---|---|---|---|
| Example 11 | 10 | 0 | 5 | 5 | 5 | 5 | 5 | 5 | 5 |
| Example 12 | 33 | 0 | 5 | 5 | 5 | 5 | 5 | 5 | 5 |
| Example 13 | 67 | 0 | 5 | 5 | 5 | 5 | 5 | 5 | 5 |
| Example 14 | 67 | 0 | 5 | 5 | 5 | 5 | 5 | 5 | 5 |
| Example 15 | 2.5 | 0 | 5 | 5 | 5 | 5 | 5 | 5 | 5 |

We claim:

1. A herbicidal composition containing a fluoropropylthiazoline derivative represented by the formula (1):

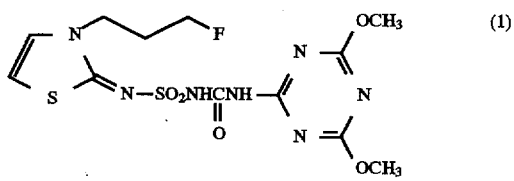

and at least one compound selected from the group consisting of compounds represented by the following formulae (2), (3), (4), (5) and (6) as active ingredients:

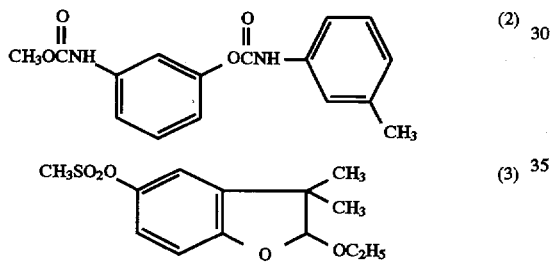

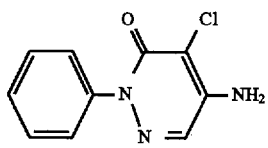

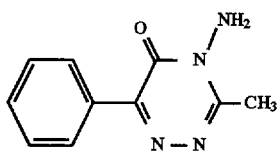

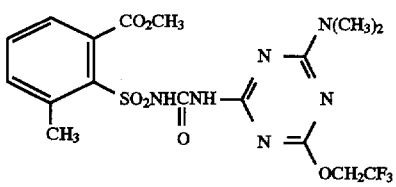

2. The herbicidal composition according to claim 1, which contains the compound represented by the formula (2) in combination with the fluoropropylthiazoline derivative.

3. The herbicidal composition according to claim 1, which contains the compound represented by the formula (3) in combination with the fluoropropylthiazoline derivative.

4. The herbicidal composition according to claim 1, which contains the compound represented by the formula (4) in combination with the fluoropropylthiazoline derivative.

5. The herbicidal composition according to claim 1, which contains the compound represented by the formula (5) in combination with the fluoropropylthiazoline derivative.

6. The herbicidal composition according to claim 1, which contains the compound represented by the formula (6) in combination with the fluoropropylthiazoline derivative.

* * * * *

UNITED STATES PATENT AND TRADEMARK OFFICE
CERTIFICATE OF CORRECTION

PATENT NO. : 5,691,276
DATED : November 25, 1997
INVENTOR(S) : Yoichi ITO et al.

It is certified that error appears in the above-identified patent and that said Letters Patent is hereby corrected as shown below:

On the title page, Item [73] and Item [87], the Assignee and the PCT Publication Number should read:

-- Nissan Chemical Industries, Ltd. --

-- PCT Pub. No.: WO96/00009
   PCT Pub. Date: Jan. 4, 1996 --

Signed and Sealed this

Tenth Day of February, 1998

Attest:

BRUCE LEHMAN

Attesting Officer      Commissioner of Patents and Trademarks